United States Patent
Williams

(10) Patent No.: US 10,433,841 B2
(45) Date of Patent: Oct. 8, 2019

(54) ADAPTER ASSEMBLY FOR SURGICAL DEVICE

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 360 days.

(21) Appl. No.: 15/363,074

(22) Filed: Nov. 29, 2016

(65) Prior Publication Data

US 2017/0164946 A1  Jun. 15, 2017

Related U.S. Application Data

(60) Provisional application No. 62/265,468, filed on Dec. 10, 2015.

(51) Int. Cl.
| | | |
|---|---|---|
| A61B 17/00 | (2006.01) | |
| A61B 17/072 | (2006.01) | |
| A61B 17/295 | (2006.01) | |
| A61B 17/115 | (2006.01) | |

(52) U.S. Cl.
CPC .... *A61B 17/07207* (2013.01); *A61B 17/1155* (2013.01); *A61B 17/295* (2013.01); *A61B 2017/0046* (2013.01); *A61B 2017/00398* (2013.01); *A61B 2017/00473* (2013.01); *A61B 2017/00477* (2013.01); *A61B 2017/07257* (2013.01); *A61B 2017/07285* (2013.01)

(58) Field of Classification Search
CPC .......... A61B 17/07207; A61B 17/1155; A61B 17/295; A61B 2017/00398; A61B 2017/0046; A61B 2017/00473; A61B 2017/00477; A61B 2017/07257; A61B 2017/07285; A61B 2017/00371; A61B 2017/2903; A61B 2017/00486; A61F 2002/30525; F16H 37/122
USPC ........................................... 227/175.1; 74/25
See application file for complete search history.

(56) References Cited

U.S. PATENT DOCUMENTS

| | | | |
|---|---|---|---|
| 2,669,135 A * | 2/1954 | Moore | B23Q 1/267 408/128 |
| 2,777,340 A | 1/1957 | Hettwer et al. | |
| 2,957,353 A | 10/1960 | Babacz | |
| 3,111,328 A | 11/1963 | Di Rito et al. | |

(Continued)

FOREIGN PATENT DOCUMENTS

| | | |
|---|---|---|
| CA | 2451558 A1 | 1/2003 |
| CN | 1547454 A | 11/2004 |

(Continued)

OTHER PUBLICATIONS

European Search Report dated Apr. 18, 2017, issued in EP Application No. 16203270.

(Continued)

*Primary Examiner* — Hemant Desai
*Assistant Examiner* — Amelia Jae-Ippel Vorce

(57) ABSTRACT

An adapter assembly for connecting an end effector to an electromechanical surgical instrument includes first, second, and third drive assemblies configured for converting rotational motion into linear motion. Each of the second and third drive assemblies includes a jackscrew assembly for longitudinally advancing and retracting respective second and third drive members.

20 Claims, 14 Drawing Sheets

(56) References Cited

U.S. PATENT DOCUMENTS

| | | | |
|---|---|---|---|
| 3,409,090 A * | 11/1968 | Brown | B23Q 5/261 173/141 |
| 3,695,058 A | 10/1972 | Keith, Jr. | |
| 3,734,515 A | 5/1973 | Dudek | |
| 3,759,336 A | 9/1973 | Marcovitz et al. | |
| 4,090,803 A * | 5/1978 | Haley | B23B 39/165 408/103 |
| 4,162,399 A | 7/1979 | Hudson | |
| 4,203,570 A * | 5/1980 | Hurley | F16K 3/182 251/14 |
| 4,606,343 A | 8/1986 | Conta et al. | |
| 4,705,038 A | 11/1987 | Sjostrom et al. | |
| 4,722,685 A | 2/1988 | de Estrada et al. | |
| 4,823,807 A | 4/1989 | Russell et al. | |
| 4,874,181 A | 10/1989 | Hsu | |
| 5,129,118 A | 7/1992 | Walmesley | |
| 5,129,570 A | 7/1992 | Schulze et al. | |
| 5,152,744 A | 10/1992 | Krause et al. | |
| 5,301,061 A | 4/1994 | Nakada et al. | |
| 5,312,023 A | 5/1994 | Green et al. | |
| 5,326,013 A | 7/1994 | Green et al. | |
| 5,350,355 A | 9/1994 | Sklar | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,411,508 A | 5/1995 | Bessler et al. | |
| 5,413,267 A | 5/1995 | Solyntjes et al. | |
| 5,427,087 A | 6/1995 | Ito et al. | |
| 5,433,721 A | 7/1995 | Hooven et al. | |
| 5,467,911 A | 11/1995 | Tsuruta et al. | |
| 5,476,379 A | 12/1995 | Disel | |
| 5,487,499 A | 1/1996 | Sorrentino et al. | |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,540,375 A | 7/1996 | Bolanos et al. | |
| 5,540,706 A | 7/1996 | Aust et al. | |
| 5,542,594 A | 8/1996 | McKean et al. | |
| 5,549,637 A | 8/1996 | Crainich | |
| 5,553,675 A | 9/1996 | Pitzen et al. | |
| 5,562,239 A | 10/1996 | Boiarski et al. | |
| 5,564,615 A | 10/1996 | Bishop et al. | |
| 5,609,560 A | 3/1997 | Ichikawa et al. | |
| 5,626,587 A | 5/1997 | Bishop et al. | |
| 5,632,432 A | 5/1997 | Schulze et al. | |
| 5,645,209 A | 7/1997 | Green et al. | |
| 5,647,526 A | 7/1997 | Green et al. | |
| 5,653,374 A | 8/1997 | Young et al. | |
| 5,658,300 A | 8/1997 | Bito et al. | |
| 5,662,662 A | 9/1997 | Bishop et al. | |
| 5,667,517 A | 9/1997 | Hooven | |
| 5,693,042 A | 12/1997 | Boiarski et al. | |
| 5,704,534 A | 1/1998 | Huitema et al. | |
| 5,713,505 A | 2/1998 | Huitema | |
| 5,762,603 A | 6/1998 | Thompson | |
| 5,779,130 A | 7/1998 | Alesi et al. | |
| 5,782,396 A | 7/1998 | Mastri et al. | |
| 5,782,397 A | 7/1998 | Koukline | |
| 5,792,573 A | 8/1998 | Pitzen et al. | |
| 5,797,536 A | 8/1998 | Smith et al. | |
| 5,820,009 A | 10/1998 | Melling et al. | |
| 5,863,159 A | 1/1999 | Lasko | |
| 5,908,427 A | 6/1999 | McKean et al. | |
| 5,954,259 A | 9/1999 | Viola et al. | |
| 5,964,774 A | 10/1999 | McKean et al. | |
| 5,993,454 A | 11/1999 | Longo | |
| 6,010,054 A | 1/2000 | Johnson et al. | |
| 6,017,354 A | 1/2000 | Culp et al. | |
| 6,032,849 A | 3/2000 | Mastri et al. | |
| 6,045,560 A | 4/2000 | McKean et al. | |
| 6,090,123 A | 7/2000 | Culp et al. | |
| 6,126,651 A | 10/2000 | Mayer | |
| 6,129,547 A | 10/2000 | Cise et al. | |
| 6,165,169 A | 12/2000 | Panescu et al. | |
| 6,239,732 B1 | 5/2001 | Cusey | |
| 6,241,139 B1 | 6/2001 | Milliman et al. | |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,343,731 B1 | 2/2002 | Adams et al. | |
| 6,348,061 B1 | 2/2002 | Whitman | |
| 6,368,324 B1 | 4/2002 | Dinger et al. | |
| 6,371,909 B1 | 4/2002 | Hoeg et al. | |
| 6,434,507 B1 | 8/2002 | Clayton et al. | |
| 6,443,973 B1 | 9/2002 | Whitman | |
| 6,461,372 B1 | 10/2002 | Jensen et al. | |
| 6,488,197 B1 | 12/2002 | Whitman | |
| 6,491,201 B1 | 12/2002 | Whitman | |
| 6,533,157 B1 | 3/2003 | Whitman | |
| 6,537,280 B2 | 3/2003 | Dinger et al. | |
| 6,610,066 B2 | 8/2003 | Dinger et al. | |
| 6,611,793 B1 | 8/2003 | Burnside et al. | |
| 6,645,218 B1 | 11/2003 | Cassidy et al. | |
| 6,654,999 B2 | 12/2003 | Stoddard et al. | |
| 6,698,643 B2 | 3/2004 | Whitman | |
| 6,699,177 B1 | 3/2004 | Wang et al. | |
| 6,716,233 B1 | 4/2004 | Whitman | |
| 6,743,240 B2 | 6/2004 | Smith et al. | |
| 6,783,533 B2 | 8/2004 | Green et al. | |
| 6,792,390 B1 | 9/2004 | Burnside et al. | |
| 6,793,652 B1 | 9/2004 | Whitman et al. | |
| 6,817,508 B1 | 11/2004 | Racenet et al. | |
| 6,830,174 B2 | 12/2004 | Hillstead et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,860,892 B1 | 3/2005 | Tanaka et al. | |
| 6,899,538 B2 | 5/2005 | Matoba | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,981,628 B2 | 1/2006 | Wales | |
| 6,981,941 B2 | 1/2006 | Whitman et al. | |
| 6,986,451 B1 | 1/2006 | Mastri et al. | |
| 6,988,649 B2 | 1/2006 | Shelton, IV et al. | |
| 7,032,798 B2 | 4/2006 | Whitman et al. | |
| RE39,152 E | 6/2006 | Aust et al. | |
| 7,055,731 B2 | 6/2006 | Shelton, IV et al. | |
| 7,059,508 B2 | 6/2006 | Shelton, IV et al. | |
| 7,077,856 B2 | 7/2006 | Whitman | |
| 7,111,769 B2 | 9/2006 | Wales et al. | |
| 7,122,029 B2 | 10/2006 | Koop et al. | |
| 7,140,528 B2 | 11/2006 | Shelton, IV | |
| 7,141,049 B2 | 11/2006 | Stern et al. | |
| 7,143,923 B2 | 12/2006 | Shelton, IV et al. | |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,172,104 B2 | 2/2007 | Scirica et al. | |
| 7,225,964 B2 | 6/2007 | Mastri et al. | |
| 7,238,021 B1 | 7/2007 | Johnson | |
| 7,246,734 B2 | 7/2007 | Shelton, IV | |
| 7,252,660 B2 | 8/2007 | Kunz | |
| 7,328,828 B2 | 2/2008 | Ortiz et al. | |
| 7,364,061 B2 | 4/2008 | Swayze et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,407,078 B2 | 8/2008 | Shelton, IV et al. | |
| 7,416,101 B2 | 8/2008 | Shelton, IV et al. | |
| 7,419,080 B2 | 9/2008 | Smith et al. | |
| 7,422,139 B2 | 9/2008 | Shelton, IV et al. | |
| 7,431,189 B2 | 10/2008 | Shelton, IV et al. | |
| 7,441,684 B2 | 10/2008 | Shelton, IV et al. | |
| 7,448,525 B2 | 11/2008 | Shelton, IV et al. | |
| 7,464,846 B2 | 12/2008 | Shelton, IV et al. | |

(56) References Cited

U.S. PATENT DOCUMENTS

| | | |
|---|---|---|
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,573,465 B2 * | 11/2013 | Shelton, IV ......... A61B 17/072 227/180.1 |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,747,238 B2 * | 6/2014 | Shelton, IV ........... B23K 26/38 464/149 |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |

(56) References Cited

U.S. PATENT DOCUMENTS

| | | |
|---|---|---|
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0274883 A1* | 10/2013 | McLuen .................. A61F 2/447 623/17.16 |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1* | 6/2015 | Zergiebel ......... A61B 17/07207 74/405 |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0250467 A1* | 9/2015 | Higgins ............. A61B 17/0206 600/215 |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1* | 11/2015 | Kostrzewski ...... A61B 17/0469 606/144 |
| 2015/0342601 A1 | 12/2015 | Williams et al. |
| 2015/0342603 A1 | 12/2015 | Zergiebel et al. |
| 2015/0351769 A1* | 12/2015 | Lee .................... A61B 17/1155 227/179.1 |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |

(56) References Cited

U.S. PATENT DOCUMENTS

| | | | |
|---|---|---|---|
| 2016/0106406 A1 | 4/2016 | Cabrera et al. | |
| 2016/0113648 A1 | 4/2016 | Zergiebel et al. | |
| 2016/0113649 A1 | 4/2016 | Zergiebel et al. | |

FOREIGN PATENT DOCUMENTS

| | | | |
|---|---|---|---|
| CN | 1957854 | A | 5/2007 |
| CN | 101495046 | A | 7/2009 |
| CN | 102247182 | A | 11/2011 |
| DE | 102008053842 | A1 | 5/2010 |
| EP | 0705571 | A1 | 4/1996 |
| EP | 1563793 | A1 | 8/2005 |
| EP | 1769754 | A1 | 4/2007 |
| EP | 2316345 | A1 | 5/2011 |
| EP | 2668910 | A2 | 12/2013 |
| ES | 2333509 | A1 | 2/2010 |
| JP | 2005-125075 | A | 5/2005 |
| KR | 20120022521 | A | 3/2012 |
| WO | 2011/108840 | A2 | 9/2011 |
| WO | 2012/040984 | A1 | 4/2012 |

OTHER PUBLICATIONS

Extended European Search Report corresponding to counterpart International Application No. EP 14 18 4882.0 dated May 12, 2015.
Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 9783.3 dated Sep. 3, 2015.
Extended European Search Report corresponding to counterpart International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
Australian Examination Report No. 1 corresponding to International Application No. AU 2013205872 dated Oct. 19, 2016.
Australian Examination Report from Appl. No. AU 2013205840 dated Nov. 3, 2016.
European Search Report corresponding to EP 15 184 915.5-1654 dated Sep. 16, 2016.

* cited by examiner

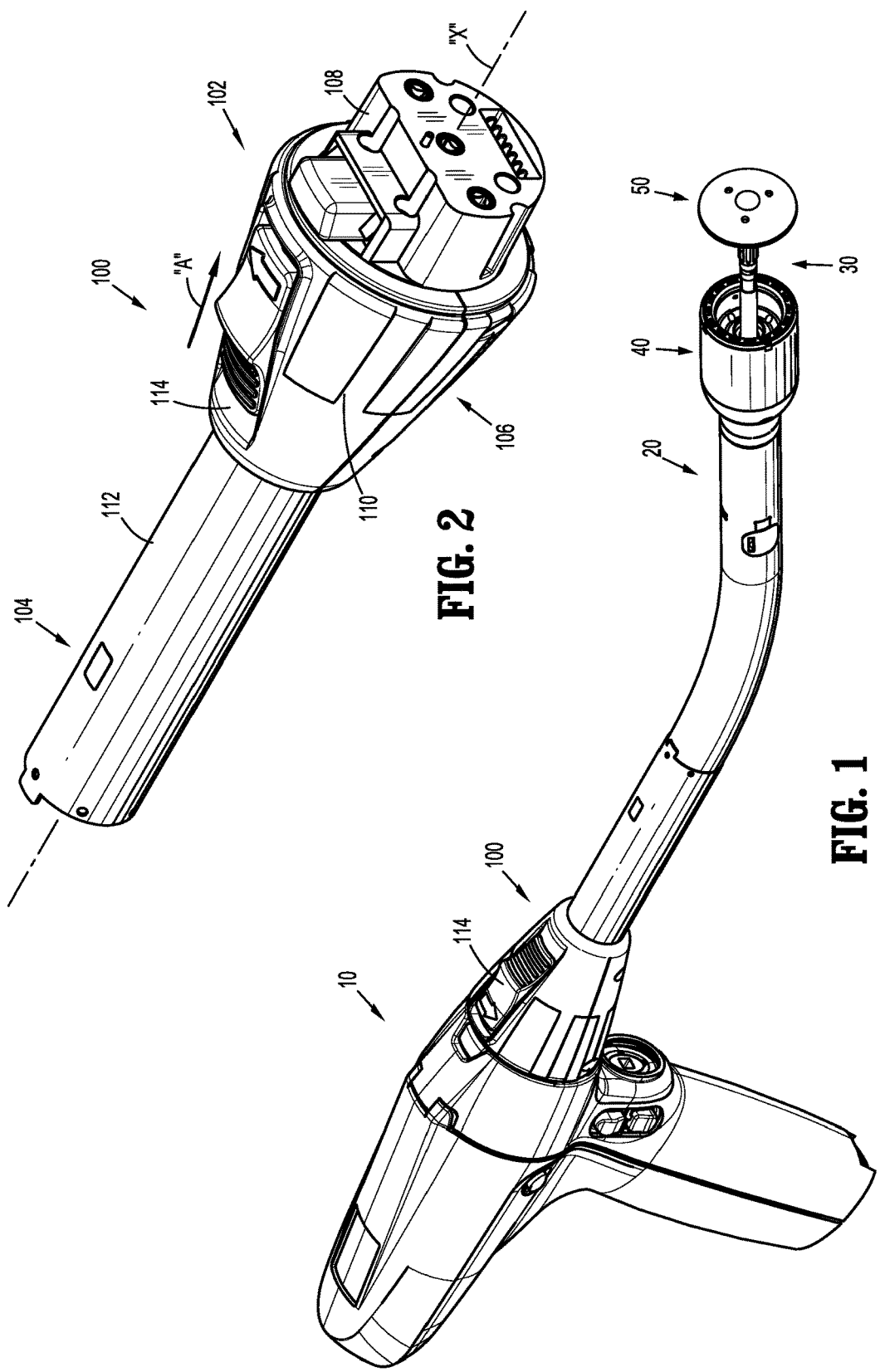

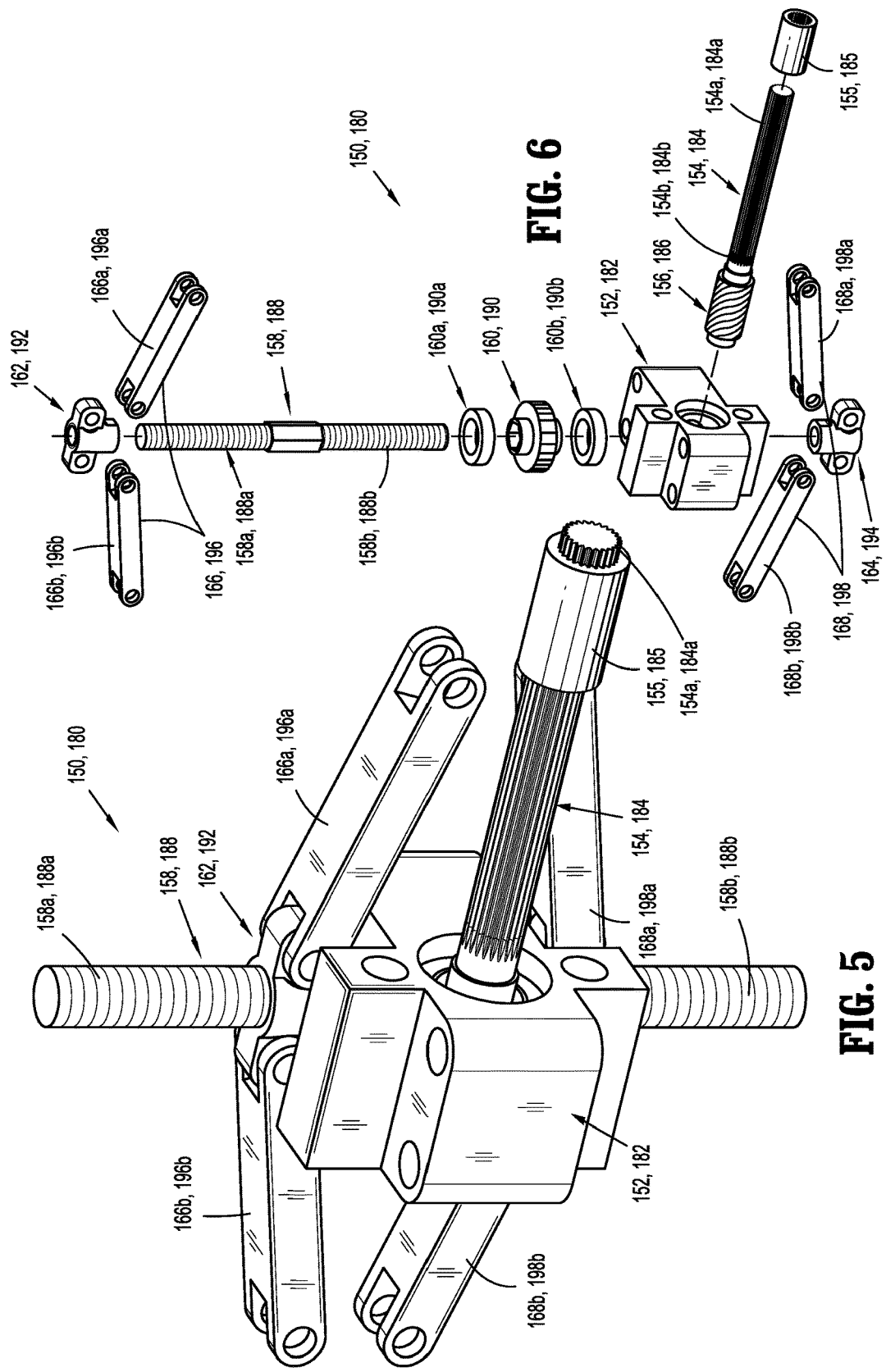

ADAPTER ASSEMBLY FOR SURGICAL DEVICE

CROSS-REFERENCE TO RELATED APPLICATIONS

This application claims the benefit of and priority to U.S. Provisional Patent Application No. 62/265,468, filed Dec. 10, 2015, the entire disclosure of which is incorporated by reference herein.

BACKGROUND

1. Technical Field

The present disclosure relates generally to powered surgical devices. More specifically, the present disclosure relates to adapter assemblies for selectively connecting end effectors to actuation units of powered surgical devices.

2. Background of Related Art

Powered devices for use in surgical procedures typically convert rotational motion from the handle assembly to linear motion for effectuating one or more functions, e.g., clamping, stapling, cutting. To permit reuse of the handle assemblies of these powered surgical devices and so that the handle assembly may be used with a variety of end effectors, adapter assemblies have been developed for selective attachment to the handle assemblies and to a variety of end effectors. Following use, the adapter assembly may be disposed of along with the end effector. In some instances, the adapter assembly may be sterilized for reuse.

SUMMARY

An adapter assembly for operably connecting an end effector to a powered surgical instrument is provided. The adapter assembly includes a drive coupling assembly, a first drive assembly, a second drive assembly, and a third drive assembly. The first drive assembly includes a drive screw and is operably connected to the drive coupling assembly for effectuating a first function. The second drive assembly includes a first jackscrew assembly and is operably connected to the drive coupling assembly for effectuating a second function. The third drive assembly includes a second jackscrew assembly and is operably connected to the drive coupling assembly for effectuating a third function.

In some embodiments, the second drive assembly includes a second drive member operably connected to the first jackscrew assembly. The first jackscrew assembly may be movable from a collapsed configuration to an extended configuration to move the second drive member from a proximal position to a distal position. Similarly, the third drive assembly may include a third drive member operably connected to the second jackscrew assembly. The second jackscrew assembly may be movable from a collapsed configuration to an extended configuration to move the third drive member from a proximal position to a distal position. Each of the second and third drive members may include a tubular portion. The tubular portion of the third drive member may be slidably disposed within the tubular portion of the second drive member. Each of the second and third drive assemblies may include a guide member, and each of the second and third drive members may include a guide portion slidably disposed within the respective guide members. The first drive member may be slidably disposed within the tubular portion of the second drive member.

In embodiments, the drive coupling assembly includes a thruster plate and first, second, and third connector members. The first connector member may be operably connected to the drive screw. The second connector member may be operably connected to the first jackscrew assembly. The third connector member may be operably connected to the second jackscrew assembly.

The first jackscrew assembly may include a housing, a drive shaft rotatably received within the housing, a worm drive operably disposed on the drive shaft, a jackscrew received within the housing and extending perpendicular to the drive shaft, a worm gear operably disposed about the jackscrew, first and second jackscrew carriers operably received on the jackscrew, and first and second link assemblies pivotally connected to the respective first and second jackscrew carriers. Each of the first and second link assemblies may include first and second links. The first and second links of each of the first and second link assemblies may define a first angle therebetween when the first jackscrew is in a collapsed configuration. The first and second links of each of the first and second link assemblies may define a second angle therebetween when the first jackscrew is in an extended configuration. The second angle may be greater than the first angle.

The first jackscrew assembly may define a first effective length when the first jackscrew assembly is in a collapsed configuration and the first jackscrew assembly may define a second effective length when the first jackscrew assembly is in the extended configuration. The second effective length may be greater than the first effective length.

In embodiments of an adapter assembly, the first function is the clamping of tissue, the second function is the stapling of the tissue, and the third function is the cutting of the tissue. The adapter assembly may further include a rotation assembly including a base, a rotation handle rotatably secured to the base, and a sleeve fixedly secured to the rotation handle. The first, second, and third drive assemblies may be secured within the base.

BRIEF DESCRIPTION OF THE DRAWINGS

Embodiments of the present disclosure are described herein with reference to the accompanying drawings, wherein:

FIG. 1 is a perspective view of an adapter assembly, in accordance with an embodiment of the present disclosure, an exemplary electromechanical surgical device, an exemplary extension assembly, and an exemplary end effector;

FIG. 2 is a perspective view of a drive assembly of the adapter assembly of FIG. 1;

FIG. 5 is a perspective side view of a jackscrew assembly of the drive assembly of FIG. 3;

FIG. 6 is a perspective, separated side view of the jackscrew assembly of FIG. 5;

DETAILED DESCRIPTION OF EMBODIMENTS

Figure 3:
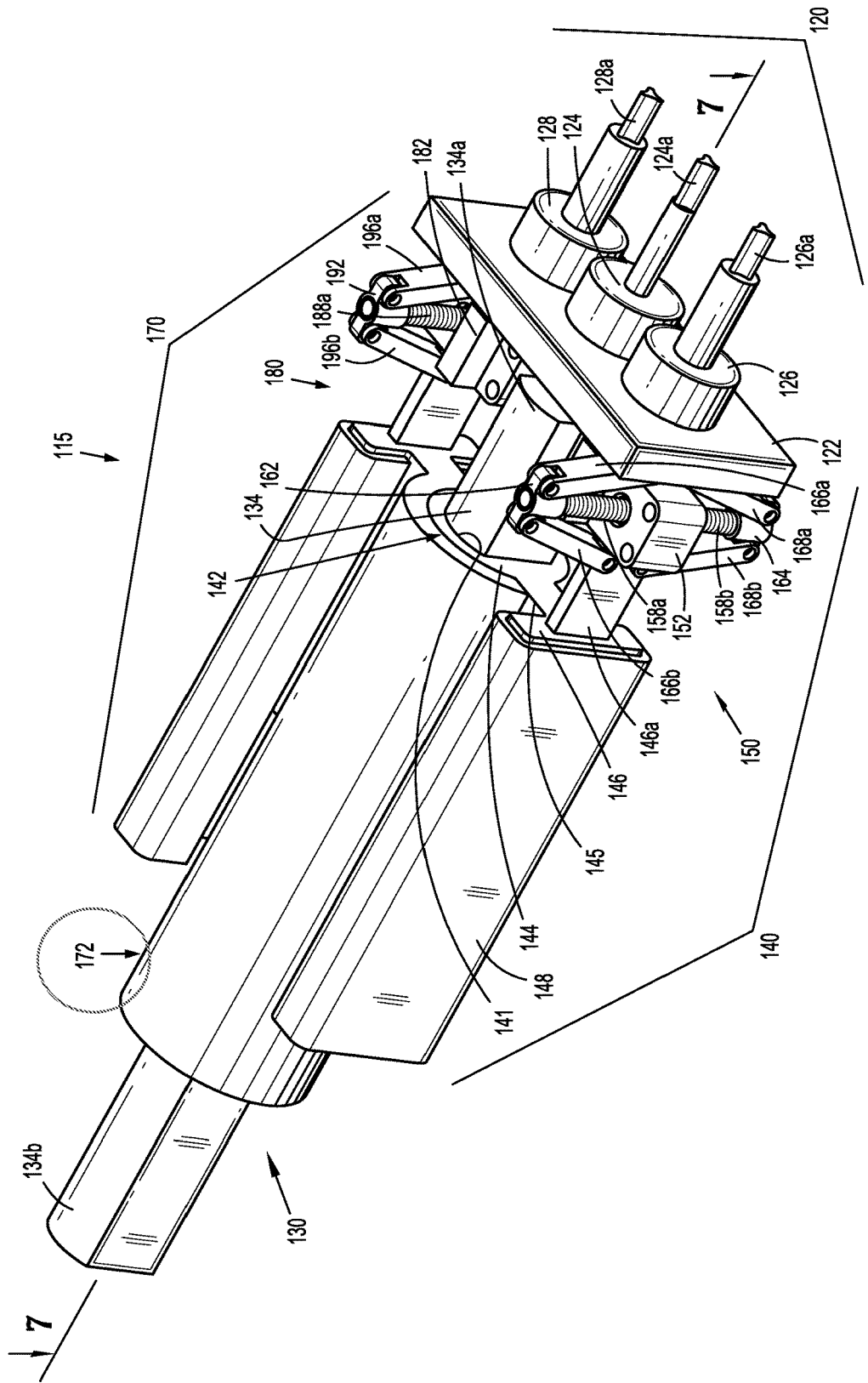
FIG. 3 is a perspective view of the drive assembly of FIG. 2.

Embodiments of the presently disclosed adapter assembly for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

With reference to FIGS. 1 and 2, an adapter assembly in accordance with an embodiment of the present disclosure, shown generally as adapter assembly 100, is configured for selective connection to a powered handheld electromechanical instrument shown, generally as surgical device 10. As illustrated in FIG. 1, the surgical device 10 is configured for selective connection with the adapter assembly 100, and, in turn, the adapter assembly 100 is configured for selective connection with an extension assembly 20. The extension assembly 20 is configured for selective connection with a tool assembly or end effector, e.g. tool assembly 30, which may, in exemplary embodiments, include a loading unit 40 and an anvil assembly 50, for applying a circular array of staples (not shown) to tissue (not shown).

For a detailed description of the structure and function of an exemplary electromechanical instrument, please refer to commonly owned U.S. Pat. Appl. Publ. No. 2012/0253329, the content of which is incorporated by reference herein in its entirety.

With continued reference to FIG. 2, the adapter assembly 100 includes a proximal portion 102 and a distal portion 104. The proximal portion 102 includes a rotation assembly 106 having a base 108, and a rotation handle 110 rotatable relative to the base 108 about a longitudinal axis "x" of the adapter assembly 100. The distal portion 104 includes a sleeve 112 fixedly secured to the rotation handle 110. Rotation of the rotation handle 110 causes rotation of the sleeve 112. In this manner, an end effector, e.g. tool assembly 30 (FIG. 1), secured to the distal portion 104 of the adapter assembly 100, or an end effector secured to an extension assembly, e.g., extension assembly 20 (FIG. 1), which is secured to the distal portion 104 of the adapter assembly 100 is rotatable about the longitudinal axis "x" independent of movement of the surgical device 10 (FIG. 1) to which adapter assembly 100 is attached.

Still referring to FIG. 2, a latch 114 is mounted to the rotation handle 110 and selectively secures the rotation handle 110 in a fixed orientation about the longitudinal axis "x". The latch 114 is configured to lock the rotation handle 110 relative to the base 108. Proximal movement of the latch 114, as indicated by arrow "A" in FIG. 2, disengages the latch 114 from the base 108 to permit rotation of the rotation handle 110 relative to the base 106. For a detailed description of an exemplary rotation assembly and latch mechanism, please refer to commonly owned U.S. Provisional Patent Application Ser. No. 62/066,518, the content of which is incorporated by reference herein in its entirety.

Figure 4:
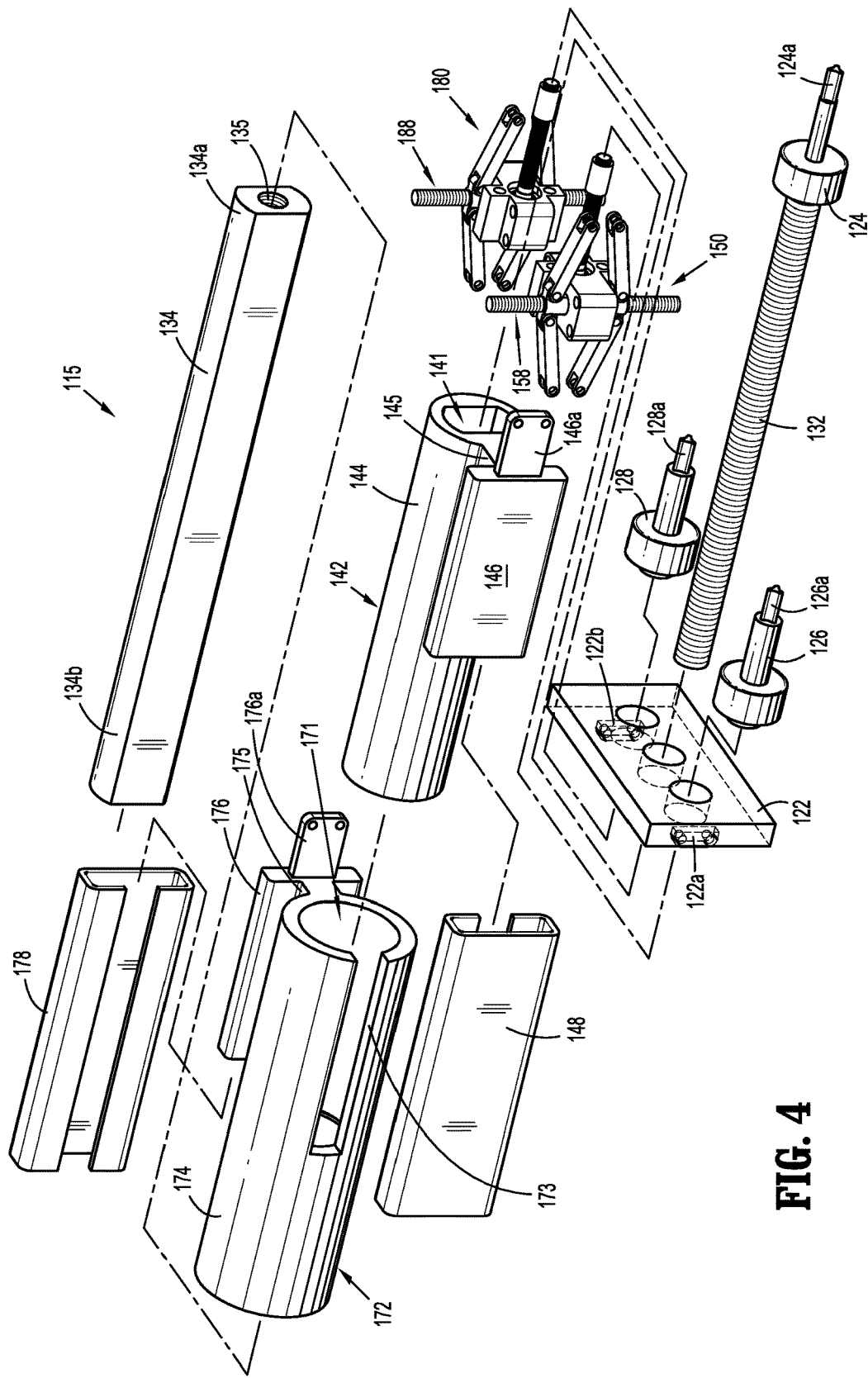
FIG. 4 is a perspective, separated view of the drive assembly of FIG. 3.

Turning now to FIGS. 3 and 4, the adapter assembly 100 (FIG. 2) includes a drive assembly 115 for effecting actuation of an end effector, e.g., tool assembly 30 (FIG. 1), secured to the distal portion 104 (FIG. 2) of the adapter assembly 100 (FIG. 1) and/or an end effector, e.g., tool assembly 30, secured to an extension assembly, e.g., the extension assembly 20 (FIG. 1), which is secured to the distal portion 104 of the adapter assembly 100. The drive assembly 115 is configured for transferring rotational motion from the surgical device 10 (FIG. 1) to linear motion to effect actuation of an end effector. More specifically, the drive assembly 115 includes a drive coupling assembly 120 (FIG. 3), and first, second, and third drive assemblies 130, 140, 170 operably connected to the drive coupling assembly 120 for transferring rotation movement of respective first, second, and third drive shafts (not shown) of the surgical device 10 (FIG. 1) to respective first, second, and third linear movement for effecting first, second, and third actuations of an attached end effector, e.g. tool assembly 30 (FIG. 1), for performing respective first, second, and third operations of the tool assembly 30, e.g., clamping, stapling, and cutting.

The drive coupling assembly 120 (FIG. 3) is operably supported within the base 108 (FIG. 1) of the rotation assembly 106 (FIG. 1) and includes a thruster plate 122, and first, second, and third connector members 124, 126, 128 rotatably supported through the thruster plate 122. The thruster plate 122 includes first and second support tabs 122a, 122b (FIG. 4; in phantom) extending distally therefrom. Proximal ends 124a, 126a, 128a of the respective first, second, and third connector members 124, 126, 128 are configured for operable connection with the respective first, second, and third drive shafts (not shown) of a surgical device, e.g., the surgical device 10 (FIG. 1).

The first drive assembly 130 (FIG. 3) includes a drive screw 132 (FIG. 4) integrally formed with or fixedly coupled to the first connector member 124 of the drive coupling assembly 120 and extending distally therefrom, and a first drive member 134 longitudinally movable relative to the drive screw 132. Specifically, a proximal end 134a of the first drive member 134 defines a threaded longitudinal opening 135 through which the drive screw 132 is received. Rotation of the drive screw 132 in a first direction causes the first drive member 134 to move proximally, i.e., retract, and rotation of the drive screw 132 in a second direction causes the first drive member 134 to move in a distal direction, i.e., advance. As will be described in further detail below, a distal end 134b of the first drive member 134 is operably connectable to a drive member (not shown) of an anvil assembly, e.g., the anvil assembly 50 (FIG. 1), of an end effector, e.g., tool assembly 30 (FIG. 1), to perform a first function, e.g., clamping of tissue.

Still referring to FIGS. 3 and 4, the second drive assembly 140 (FIG. 3) includes a second drive member 142, and a first jackscrew assembly 150 operably disposed between the second connector member 126 of the drive coupling assembly 120 and the second drive member 142. The second drive member 142 includes a tubular portion 144 and a guide portion 146 secured to the tubular portion 144 by a flange 145. A connector extension 146a extends proximally from the guide portion 146 and engages the first jackscrew assembly 150. The guide portion 146 of the second drive member 142 is slidably disposed within a first guide member 148. Although not shown, the guide member 148 is fixedly secured within the rotation handle 110 (FIG. 2) of the rotation assembly 106 (FIG. 2) and maintains the second drive member 142 in axial alignment with the longitudinal axis "x" (FIG. 2) of the adapter assembly 100 (FIG. 2) as operation of the first jackscrew assembly 150 longitudinally translates the second drive member 142. The tubular portion 144 of the second drive member 142 defines a longitudinal opening 141 through which the first drive member 134 of the first drive assembly 130 is received.

Figure 7:
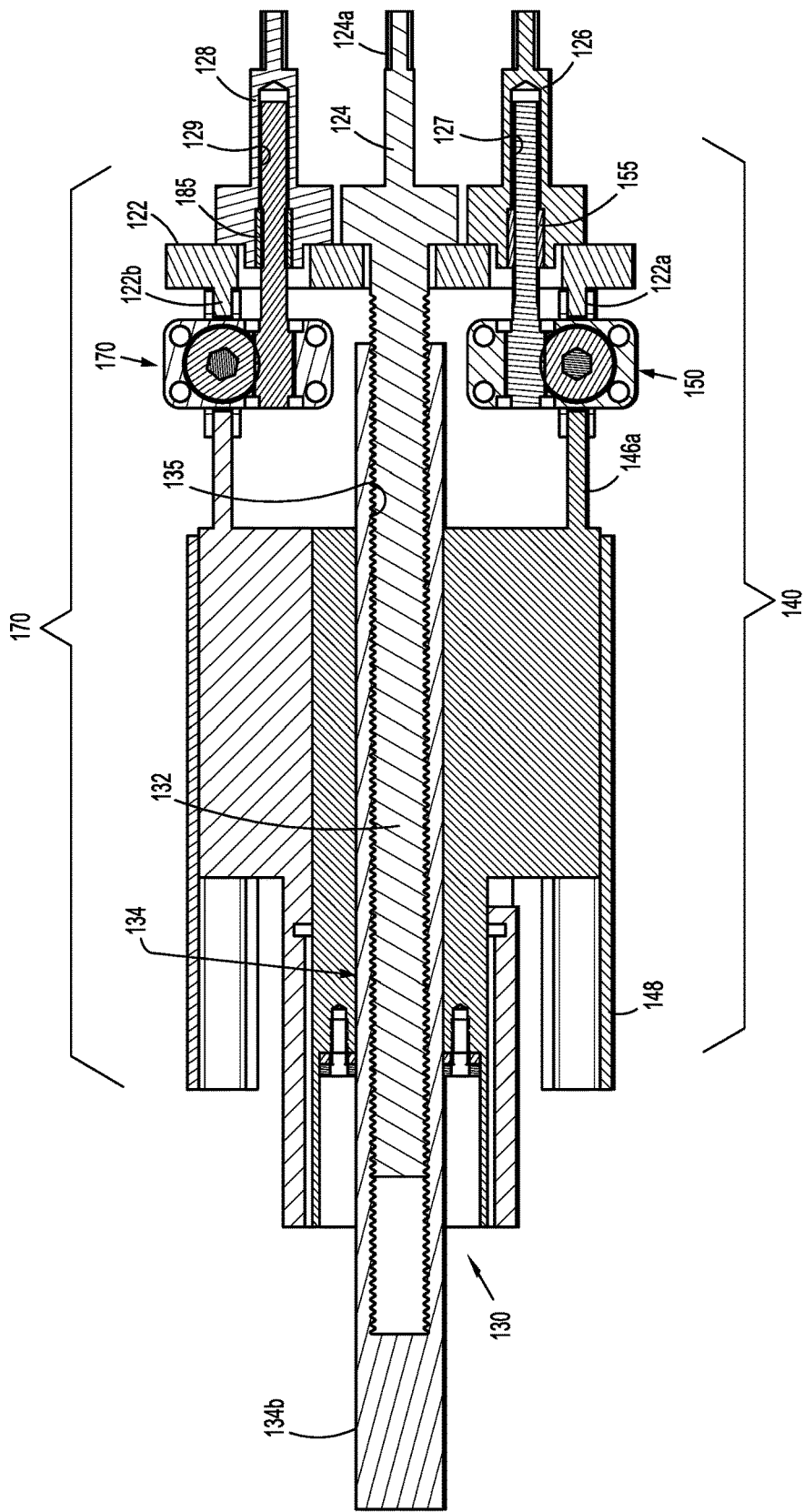
FIG. 7 is a cross-sectional top view of the drive assembly of FIG. 3 taken along line 7-7 in FIG. 3.

With reference to FIG. 5, and particular reference to FIG. 6, the first jackscrew assembly 150 includes a housing 152, a drive shaft 154, a worm drive 156 (FIG. 6) on a distal end 154b (FIG. 6) of the drive shaft 154, a jackscrew 158, a worm gear 160 (FIG. 6) supported by first and second bearing members 160a (FIG. 6), 160b (FIG. 6), first and second jackscrew carriers 162, 164 (FIG. 6), and first and second link assemblies 166 (FIG. 6), 168 (FIG. 6). A proximal end 154a of the drive shaft 154 is rotatably supported within the thruster plate 122 (FIG. 4) of the drive coupling assembly 120 (FIG. 3) by a bearing member 155 and is operably connected to the second drive connector 126 (FIG. 3) of the drive coupling assembly 120. More particularly, the proximal end 154a of the drive shaft 154 is slidably disposed and rotationally fixed within a longitudinal cavity 127 (FIG. 7) of second drive connector 126 to accommodate longitudinal movement of the first jackscrew assembly 150 during actuation of the second drive assembly 140. The distal end 154b of the drive shaft 154, including the worm drive 156, is rotatably supported within the housing 152. The jackscrew 158 is rotatably received within and through the housing 152 perpendicular to the drive shaft 154. The worm gear 160 is fixedly supported on the jackscrew 158 and operably engages the worm drive 156. As will be described in further detail below, rotation of the drive shaft 154 causes rotation of the jackscrew 158.

A first end 158a of the jackscrew 158 includes a thread formed thereabout in a first direction, e.g., right-handed thread, and a second end 158b of the jackscrew 158 includes a thread formed thereabout in a second direction, e.g., left-handed thread. The first jackscrew carrier 162 is received about the first end 158a of the jackscrew 158, and the second jackscrew carrier 164 is received about the second end 158b of the jackscrew 158. The first and second jackscrew carriers 162, 164 are configured such that rotation of the jackscrew 158 in a first direction causes the first and second jackscrew carriers 162, 164 to move towards one another i.e., towards the housing 152, and rotation of the jackscrew 158 in a second direction causes the first and second jackscrew carriers 162, 164 to move away from one another, i.e., away from the housing 152.

A first link 166a of the first link assembly 166 connects the first jackscrew carrier 162 to the thruster plate 122 (FIG. 4), and a second link 166b of the first link assembly 166 connects the first jackscrew carrier 162 to the guide portion 146 (FIG. 4) of the second drive member 142 (FIG. 4). More specifically, a proximal end of the first link 166a of the first link assembly 166 is pivotally secured to the first support tab 122a (FIG. 4) of the thruster plate 122, and a distal end of the first link 166a is pivotally secured to the first jackscrew carrier 162. A proximal end of the second link 166b of the first link assembly 166 is pivotally secured to the first jackscrew carrier 162, and a distal end of the second link 166b is pivotally secured to the connector extension 146a of the guide portion 146 of the second drive member 142.

Similarly, a first link 168a of the second link assembly 168 connects the first jackscrew carrier 162 to the thruster plate 122 (FIG. 4), and a second link 168b of the second link assembly 168 connects the second jackscrew carrier 164 to the guide portion 146 of the second drive member 142. More specifically, a proximal end of the first link 168a of the second link assembly 168 is pivotally secured to the first support tab 122a (FIG. 4) of the thruster plate 122, and a distal end of the first link 168a is pivotally secured to the second jackscrew carrier 164. A proximal end of the second link 168b of the second link assembly 168 is pivotally secured to the second jackscrew carrier 164 and a distal end of the second link 168b is pivotally secured to the connector extension 146a of the guide portion 146 of the second drive member 142.

As will be described in further detail below, when the first and second jackscrew carriers 162, 164 are positioned on extreme ends of the jackscrew 158, the first and second links 166a, 166b, 168a, 168b of the respective first and second link assemblies 166, 168 define a first angle "α1" (FIG. 10) therebetween and the proximal ends of the first links 166a, 168b of the first and second link assemblies 166, 168 and the distal ends of the second links 166b, 168b of the first and second link assemblies 166, 168 define a first distance "d1" (FIG. 10) therebetween.

When the first and second jackscrew carriers 162, 164 are positioned on the jackscrew 158 adjacent the housing 152, the first and second links 166a, 166b, 168a, 168b of the respective first and second link assemblies 166, 168 define a second angle "α2" (FIG. 14) therebetween, and the proximal ends of the first links 166a, 168b of the respective first and second link assemblies 166, 168 and the distal ends of the second links 166b, 168b of the respective first and second link assemblies 166, 168 define a second distance "d2" (FIG. 14) therebetween. The second angle "α2" is greater than the first angle "α1" and the second distance "d2" is greater than the first distance "d1". In this manner, movement of the first and second jackscrew carriers 162, 164 from the position on the extreme ends of the jackscrew 158 to the position adjacent the housing 152 increases the effective length of the jackscrew assembly 150.

With reference still to FIGS. 3 and 4, the third drive assembly 170 includes a third drive member 172, and a second jackscrew assembly 180 operably disposed between the third connector member 128 of the drive coupling assembly 120 and the third drive member 172. The third drive member 172 includes a tubular portion 174, and a guide portion 176 secured to the tubular portion by a flange portion 175. A connector extension 176a extends proximally from the guide portion 176 and engages the second jackscrew assembly 180. The guide portion 176 of the third drive member 172 is slidably disposed within a second guide member 178. Although not shown, the guide member 178 is fixedly secured within rotation handle 110 (FIG. 2) of the rotation assembly 106 (FIG. 2) and maintains the third drive member 172 in axial alignment with the longitudinal axis "x" (FIG. 2) of the adapter assembly 100 (FIG. 2) as operation of the second jackscrew assembly 180 longitudinally translates the third drive member 172.

The tubular portion 174 of the third drive member 172 defines a longitudinal opening 171 and a longitudinal slot 173 for accommodating longitudinal movement of the second drive member 142 of the second drive assembly 140 relative to the third drive member 172. Specifically, the longitudinal opening 171 in the tubular portion 174 of the third drive member 172 receives the tubular portion 144 of the second drive member 142 and the longitudinal slot 173 receives the flange 145 connecting the guide portion 146 of the second drive member 142 to the tubular portion 144. This configuration permits the tubular portion 144 of the second drive member 142 to be entirely received within the tubular portion 174 of the third drive member 172, thereby reducing the overall length of the drive assembly 115 (FIG. 3).

The second jackscrew assembly 180 is a mirror image of the first jackscrew assembly 150 and will also be described with reference to FIGS. 5 and 6. The second jackscrew assembly 180 includes a housing 182, a drive shaft 184, a worm drive 186 on a distal end 184b of the drive shaft 184, a jackscrew 188, a worm gear 190 supported by first and second bearing members 190a, 190b, first and second jackscrew carriers 192, 194, and first and second link assemblies 196, 198. A proximal end 184a of the drive shaft 184 is rotatably supported within the thruster plate 122 (FIG. 3) of the drive coupling assembly 120 (FIG. 3) by a bearing member 185 and is operably connected to the third drive connector 128 (FIG. 3) of the drive coupling assembly. More particularly, the proximal end 184a of the drive shaft 184 is slidably disposed and rotationally fixed within a longitudinal cavity 129 (FIG. 7) of third drive connector 128 to accommodate longitudinal movement of the second jackscrew assembly 180 during actuation of the third drive assembly 170. The distal end 174b of the drive shaft 184, including the worm drive 186, is rotatably supported within the housing 182. The jackscrew 188 is rotatably received through the housing 182 perpendicular to the drive shaft 184. The worm gear 190 is supported on the jackscrew 188 and operably engages the worm drive 186. As will be described in further detail below, rotation of the drive shaft 184 causes rotation of the jackscrew 188.

A first end 188a of the jackscrew 188 includes a thread formed thereabout in a first direction, e.g., right-handed thread, and a second end 188b of the jackscrew 188 includes a thread formed thereabout in a second direction, e.g., left-handed thread. The first jackscrew carrier 192 is received about the first end 188a of the jackscrew 188, and the second jackscrew carrier 194 is received about the second end 188b of the jackscrew 188. The first and second jackscrew carriers 192, 194 are configured such that rotation of the jackscrew 188 in a first direction causes the first and second jackscrew carriers 192, 194 to move towards each other, i.e., towards the housing 182, and rotation of the jackscrew 188 in a second direction causes the first and second jackscrew carriers 192, 194 to move away from each other, i.e., away from the housing 182.

A first link 196a of the first link assembly 196 connects the first jackscrew carrier 192 to the thruster plate 122 (FIG. 4), and a second link 196b of the first link assembly 196 connects the first jackscrew carrier 192 to the guide portion 176 of the second drive member 172. Specifically, a proximal end of the first link 196a of the first link assembly 196 is pivotally secured to the second support tab 122b (FIG. 4) of the thruster plate 122, and a distal end of the first link 196a is pivotally secured to the first jackscrew carrier 192. A proximal end of the second link 196b of the first link assembly 196 is pivotally secured to the first jackscrew carrier 192, and a distal end of the second link 196b is pivotally secured to the connector extension 176a of the guide portion 176 of the second drive member 172.

Similarly, a first link 198a of the second link assembly 198 connects the first jackscrew carrier 192 to the thruster plate 122 (FIG. 4), and a second link 198b of the second link assembly 198 connects the second jackscrew carrier 194 to the guide portion 176 of the second drive member 172. Specifically, a proximal end of the first link 198a of the second link assembly 198 is pivotally secured to the second support tab 122b of the thruster plate 122 and a distal end of the first link 198a is pivotally secured to the second jackscrew carrier 194. A proximal end of the second link 198b of the second link assembly 198 is pivotally secured to the second jackscrew carrier 194 and a distal end of the second link 198b is pivotally secured to the connector extension 176a of the guide portion 176 of the second drive member 172.

As will be described in further detail below, when the first and second jackscrew carriers 192, 194 are positioned on extreme ends of the jackscrew 188, the first and second links 196a, 196b, 198a, 198b of the respective first and second link assemblies 196, 198 define the first angle "α1" (FIG. 10) therebetween and the proximal ends of the first links 196a, 198b of the first and second link assemblies 196, 198 and the distal ends of the second links 196b, 198b of the first and second link assemblies 196, 198 define the first distance "d1" (FIG. 10) therebetween.

When the first and second jackscrew carriers 162, 164 are positioned on the jackscrew 158 adjacent the housing 152, the first and second links 166a, 166b, 168a, 168b of the respective first and second link assemblies 166, 168 define the second angle "α2" therebetween, and the proximal ends of the first links 196a, 198b of the respective first and second link assemblies 196, 198 and the distal ends of the second links 196b, 198b of the respective first and second link assemblies 196, 198 define the second distance "d2" (FIG. 14) therebetween. As noted above with respect to the first jackscrew assembly 150, the second angle "α2" is greater than the first angle "α1" and the second distance "d2" is greater than the first distance "d1". In this manner, movement of the first and second jackscrew carriers 192, 194 from the position on the extreme ends of the jackscrew 188 to the position adjacent the housing 182 increases the effective length of the jackscrew assembly 180.

Although shown being of substantially the same size and configuration, it is envisioned that the first and second jackscrew assemblies 150, 180 may be different sizes and/or include different configurations. For example, the threads on the jackscrews 158, 188 of the respective first and second jackscrew assemblies 150, 180 may include different pitches for moving the respective first and second jackscrew carriers 162, 164, 192, 194 at different rates.

Figure 8:
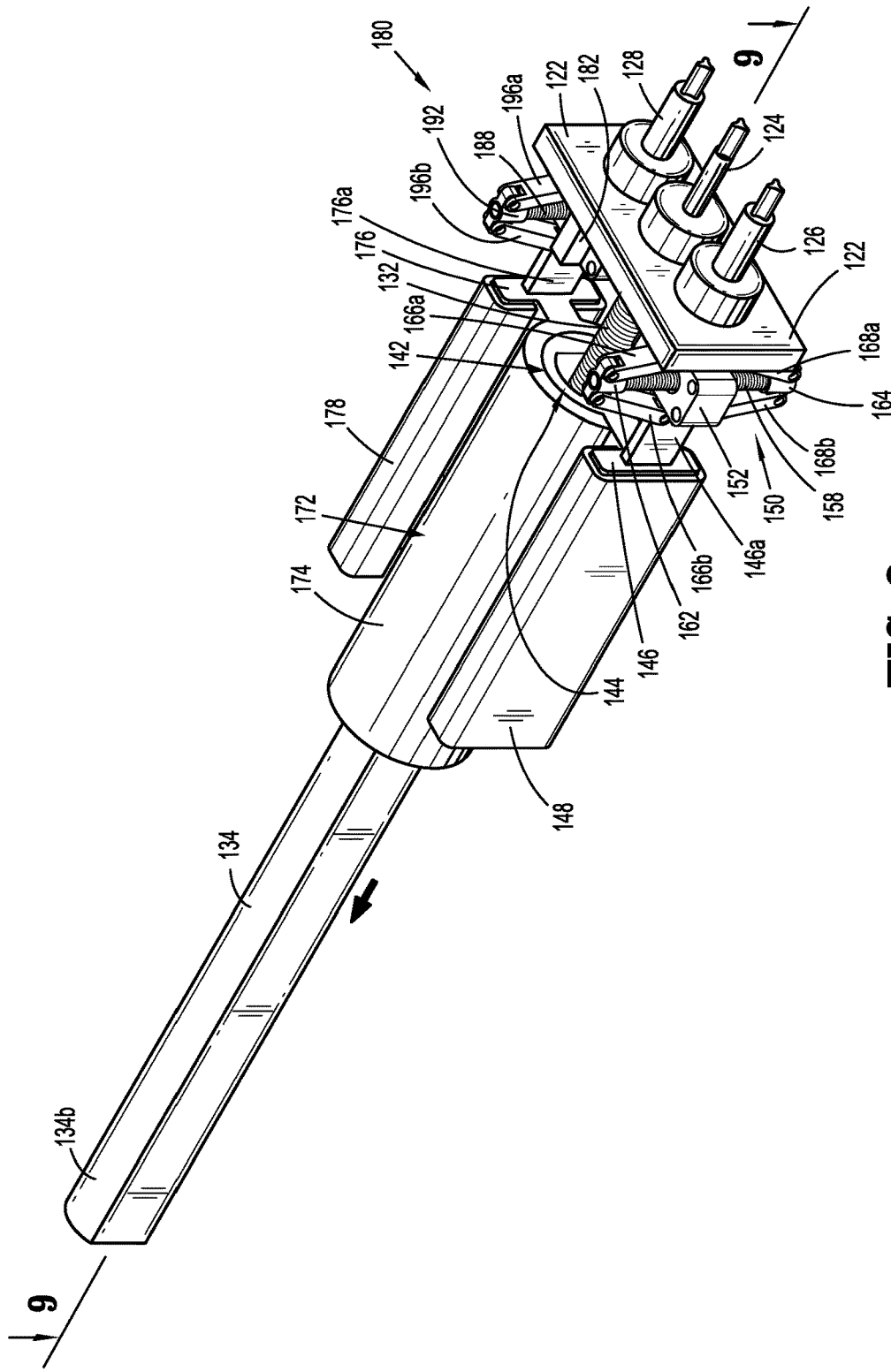
FIG. 8 is perspective view of the drive assembly of FIG. 3, with a first drive assembly in an extended position and each of a second and third drive member in a retracted position.
Figure 9:
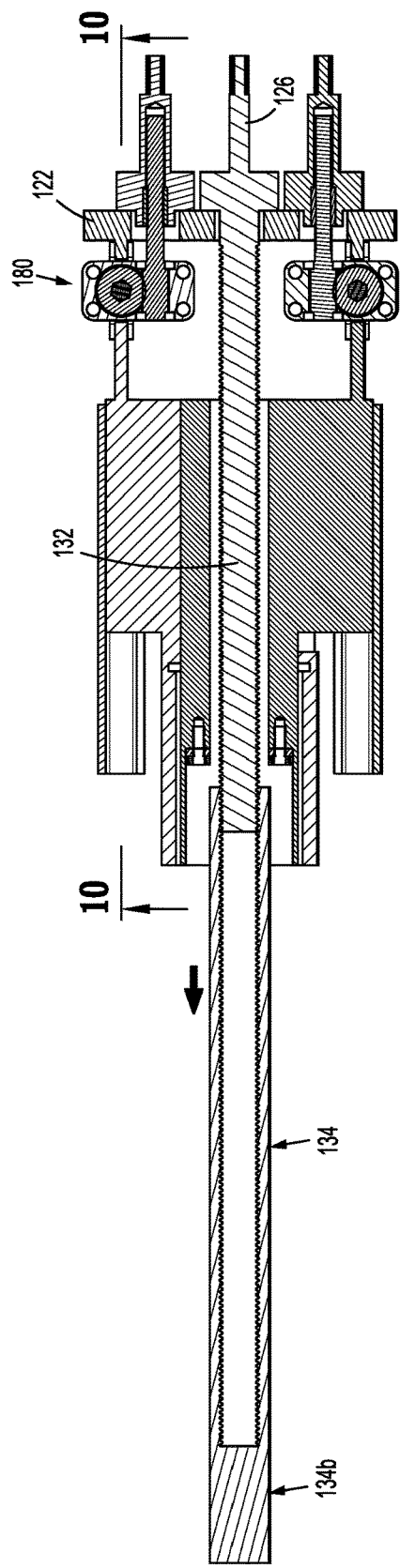
FIG. 9 is a cross-sectional top view of the drive assembly of FIG. 3 taken along line 9-9 of FIG. 8.
Figure 10:
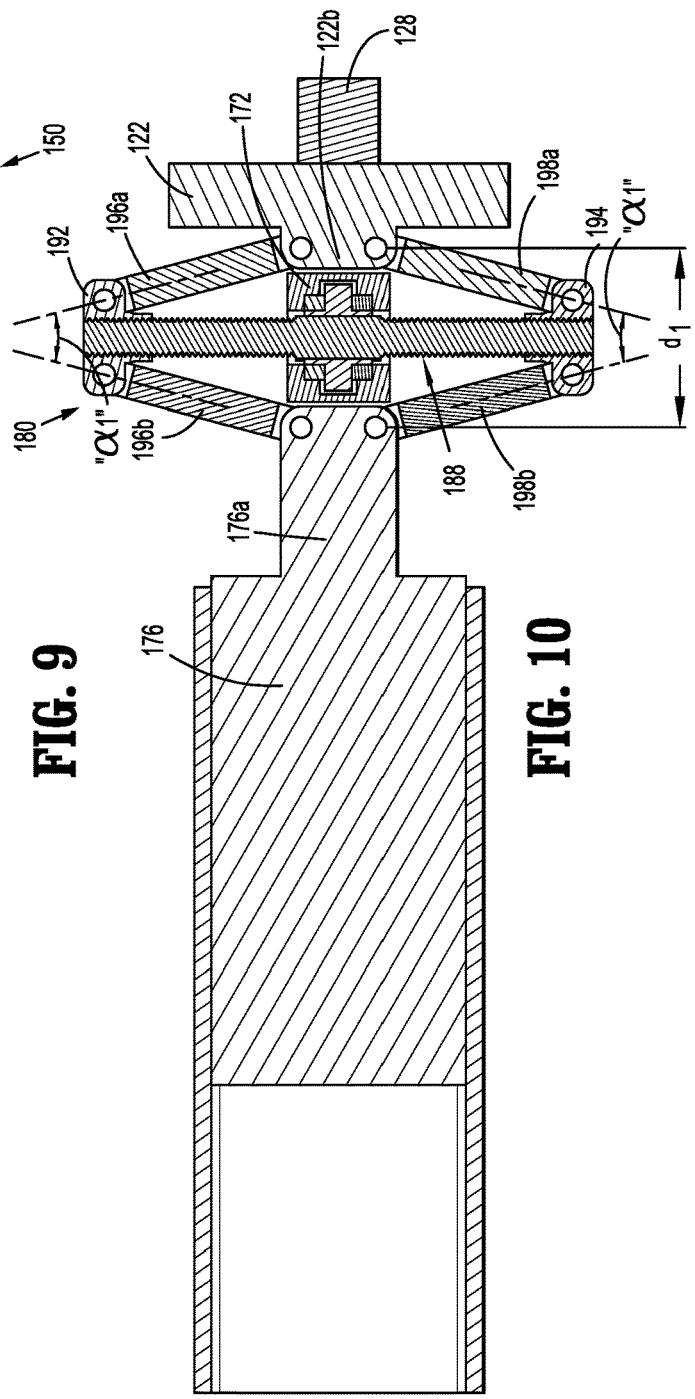
FIG. 10 is a cross-sectional side view of the drive assembly of FIG. 3 taken along line 10-10 of FIG. 9.

The operation of the drive assembly 115 will now be described with reference to FIGS. 8-17. Referring initially to FIGS. 8-10, the drive assembly 115 is shown with the first, second, and third drive assemblies 130, 140, 170 in first or initial positions. In the first positions, the first drive member 134 of the first drive assembly 130 is in a distal-most position, and each of the second and third drive members 142, 172 are in a proximal-most position. When, for example, the anvil assembly 50 (FIG. 1) of the tool assembly 30 (FIG. 1) is operably secured to the first drive member 134, in the first position, the anvil assembly 50 is spaced from the loading unit 40 (FIG. 1), as shown in FIG. 1.

Although shown and described with the first drive member 134 of the first drive assembly 130 in a distal-most position when the first drive assembly 130 is in the first position, it is envisioned that the operation of an end effector (not shown) secured to the adapter assembly 100 (FIG. 1) may require the first drive member 134 of the first drive assembly 130 to be in a proximal-most position, or at a location somewhere between the distal-most and proximal-most positions, when the first drive assembly 130 is in the first position. Similarly, although shown and described with the second and third drive members 142, 172 of the respective second and third drive assemblies 140, 170 in a proximal-most position when the second and third drive assemblies 140, 170 are in the first position, it is envisioned that the operation of an end effector secured to the adapter assembly 100 (FIG. 1) may require either or both of the second and third drive members 142, 172 of the respective second and third drive assemblies 140, 170 to be in a distal-most position, or at a location somewhere between the proximal-most and distal-most positions, when the second and/or third drive assemblies 140, 170 are in the first position.

With reference still to FIGS. 8 and 9, when the second and third drive assemblies 140, 170 are in the retracted position, the first and second jackscrew assemblies 150, 180 of the second and third drive assemblies 150, 180, respectively, are in a collapsed configuration, e.g., the first and second links 166a, 166b, 168a, 168b of the respective first and second link assemblies 166 (FIG. 6), 168 (FIG. 6) of the first jackscrew assembly 150 and the first and second links 196a, 196b, 198a, 198b of the respective first and second link assemblies 196 (FIG. 6), 198 (FIG. 6) of the second jackscrew assembly 180 define the first angle "α" (FIG. 10) therebetween. When the first and second jackscrew assemblies 150, 180 are in the collapsed configuration, the first and second jackscrew assemblies 150, 180 are positioned adjacent the thruster plate 122 and the second and third drive members 142, 172 are in their proximal-most position.

With particular reference to FIG. 10, the collapsed configuration of the second jackscrew assembly 180 will be described in detail. Although described with reference to the second jackscrew assembly 180, as noted above, the first and second jackscrew assemblies 150, 180 are mirror images of one another and operate in a substantially similar manner.

In the collapsed configuration, the first and second jackscrew carriers 192, 194 are positioned on extreme ends of the respective first and second ends 188a, 188b of the jackscrew 188. The second jackscrew assembly 180 is configured such that the proximal ends of the first links 196a, 198a of the respective first and second link assemblies 196, 198, and the distal ends of the second links 196b, 198b of the respective first and second link assemblies 196, 198 are positioned adjacent the housing 152 of the jackscrew assembly 180 when the first and second carriers 192, 194 are positioned on the extreme ends of the jackscrew 188. When in the collapsed configuration, the proximal ends of the first links 196a, 198a of the first and second link assemblies 196, 198, respectively, and the distal ends of the second links 196b, 198b of the respective first and second link assemblies 196, 198 define the distance "d1" therebetween.

Figure 11:
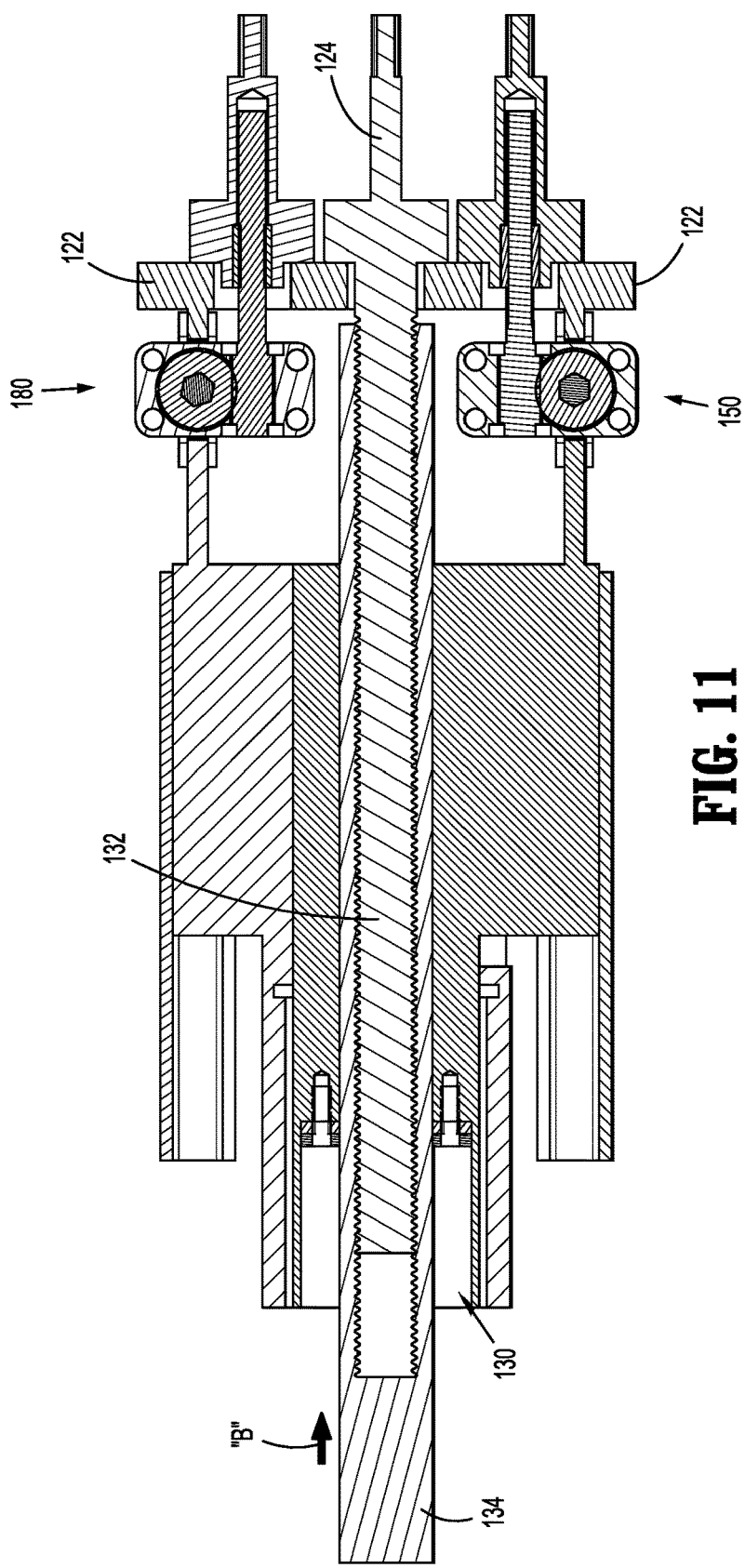
FIG. 11 is the cross-sectional side view of the drive assembly of FIG. 3 with the first drive sub-assembly in a retracted position.

Turning now to FIG. 11, movement of the first drive member 134 of the first drive assembly 130 from the first position to a second position is effected by operation of the surgical device 10 (FIG. 1). Specifically, rotation of a first drive shaft (not shown) of the surgical device 10 (FIG. 1) causes rotation of the first connector member 124 of the drive coupling assembly 120. As the first connector member 124 rotates in a first direction, the drive screw 132 secured to the first connector member 124 rotates in the same first direction within the threaded passage 135 of the first drive member 134. Rotation of the drive screw 132 within the thread passage 135 of the first drive member 134 causes the first drive member 134 to move proximally, i.e., retract, as indicated by arrow "B". Conversely, when the first connector member 124 is rotated in a second direction, the drive screw 132 rotates in the second direction to cause the first drive member 134 to move distally, i.e., advance.

Proximal movement of the first drive member 134 effectuates a first function of an end effector operably secured the adapter assembly 100 (FIG. 1). If, for example, the tool assembly 30 (FIG. 1) is operably secured to the adapter assembly 100 and the anvil assembly 50 (FIG. 1) is operably secured to the distal end 134b of the first drive member 134, proximal movement of the first drive member 134 effectuates clamping of tissue between the anvil assembly 50 and the loading unit 40 (FIG. 1).

Figure 12:
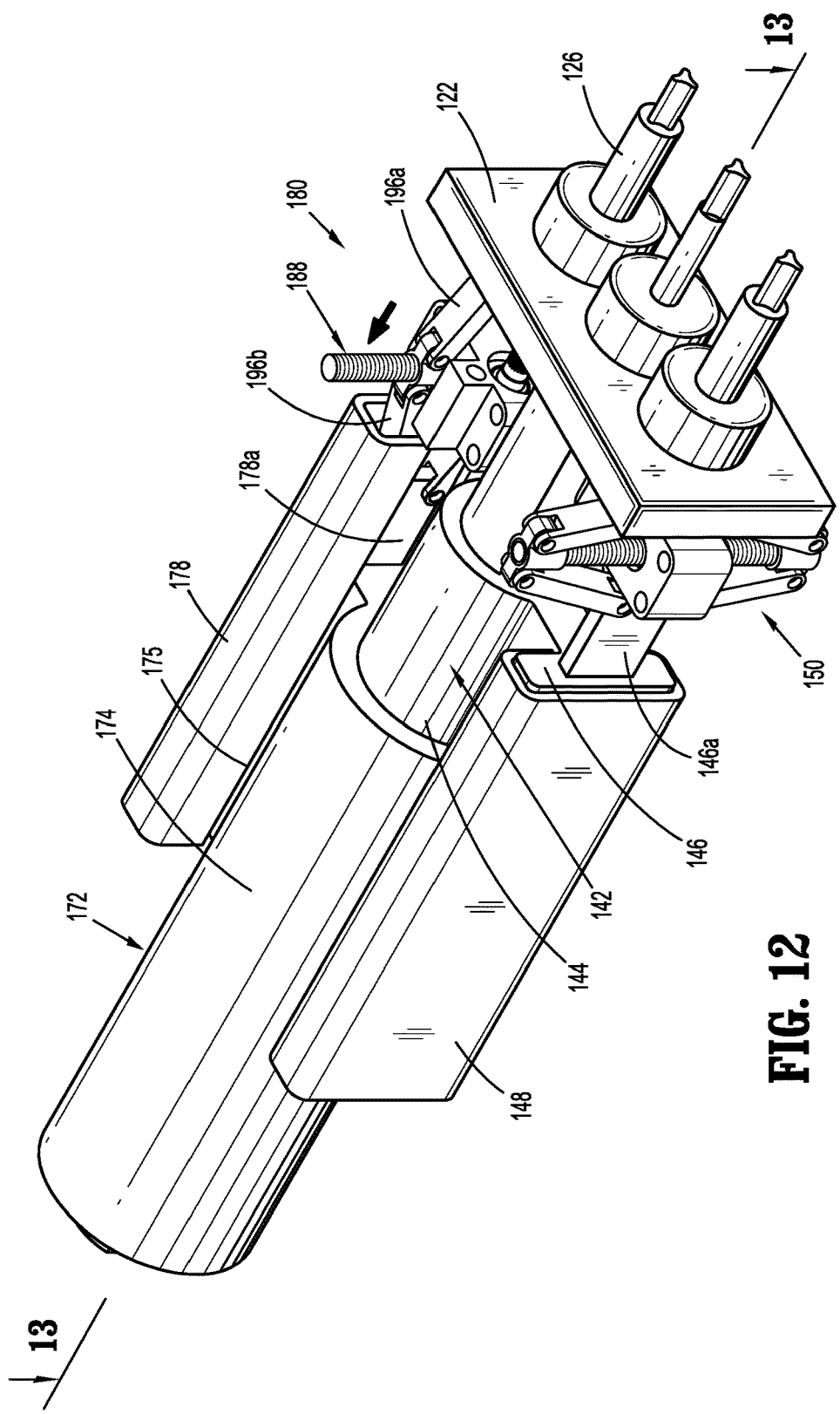
FIG. 12 is a perspective side view of the drive assembly of FIG. 3 with the first drive sub-assembly in the extended position, the second drive sub-assembly in the retracted position, and the third drive sub-assembly in the extended position.
Figure 13:
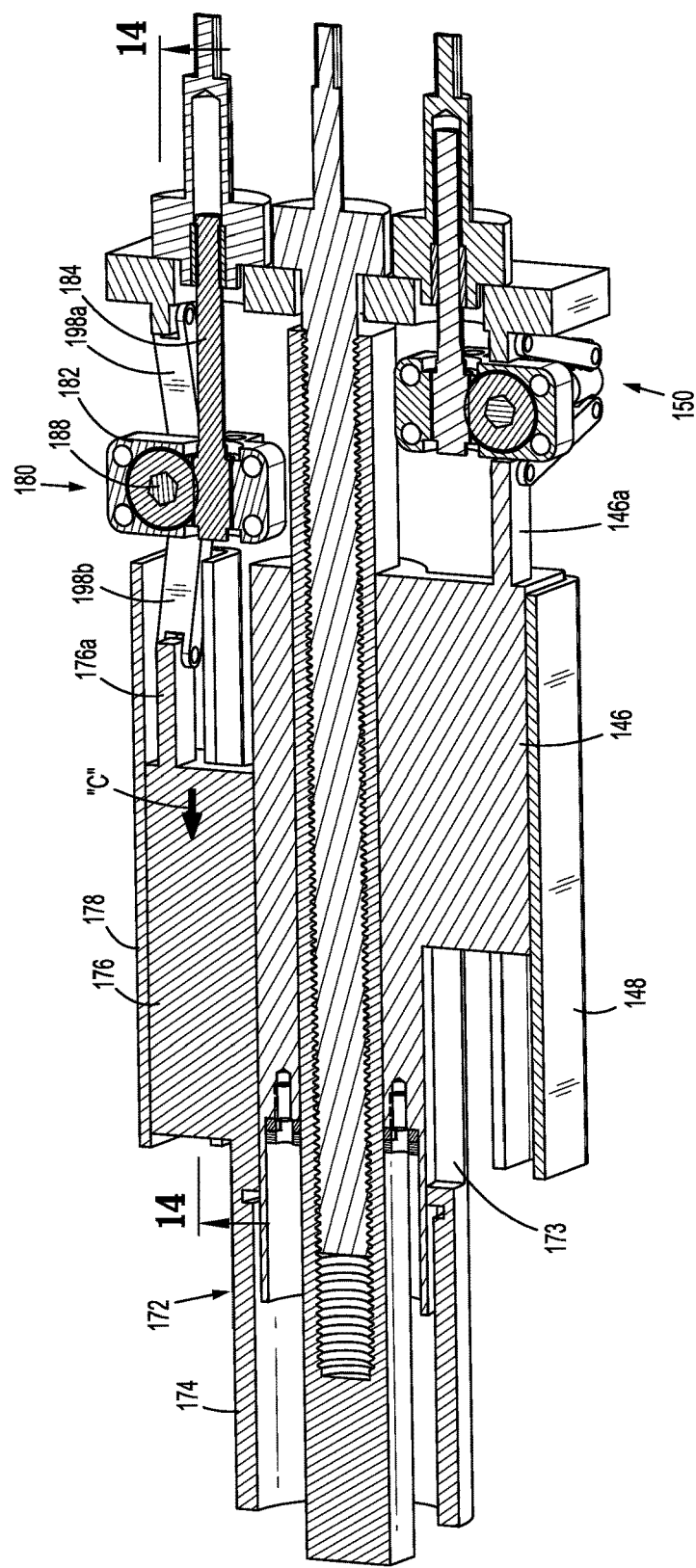
FIG. 13 is a cross-sectional top view of the drive assembly of FIG. 3 taken along line 13-13 of FIG. 12.
Figure 14:
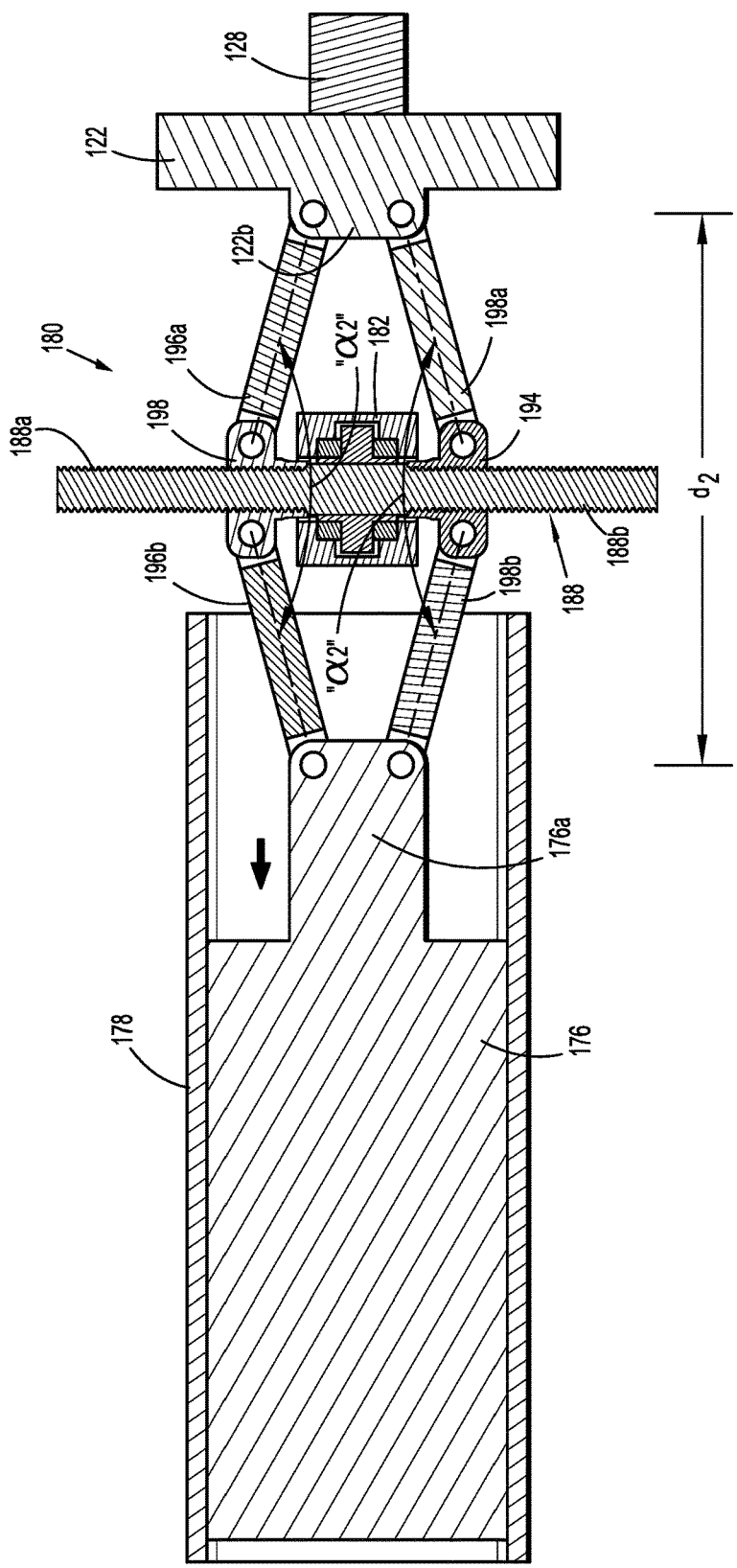
FIG. 14 is a cross-sectional side view taken along line 14-14 of FIG. 13.

Turing now to FIGS. 12-14, movement of the third drive assembly 170 from the first position to a second, extended position is effected by operation of the surgical device 10 (FIG. 1). Specifically, rotation of a third drive shaft (not shown) of the surgical device 10 (FIG. 1) causes rotation of the third connector member 128 of the drive coupling assembly 120 (FIG. 3). As the third connector member 128 rotates in a first direction, the second drive shaft 184 of the second jackscrew assembly 180 rotates in the same first direction. Rotation of the drive shaft 184 causes rotation of the jackscrew 188 of the second jackscrew assembly 180. As the jackscrew 188 rotates, the first and second jackscrew carriers 192, 194 of the second jackscrew assembly 180 move from the position on the extreme ends of the jackscrew 188 towards each other and the housing 182 of the second jackscrew assembly 180.

As the first and second jackscrew carriers 192, 194 move towards the housing 182 the angle between the first and second links 196a, 196b, 198a, 198b of respective first and second link assemblies 196, 198 of the second jackscrew assembly 180 increases, thereby increasing the effective length of the second jackscrew assembly 180 and causing the third drive member 172 of the third drive assembly 170 to move distally, as indicated by arrow "C" in FIG. 13. Conversely, when the third connector member 128 is rotated in a second direction, the drive shaft 182 rotates in the second direction to cause the jackscrew 188 to turn in the second direction which moves the first and second jackscrew carriers 192, 194 away from the housing 172 thereby causing the third drive member 174 to move proximally, i.e., retract. As noted above, the guide member 178 maintains the third drive member 172 in axial alignment with the longitudinal axis "x" (FIG. 2) of the adapter assembly 100 (FIG. 2) during translation of the third drive member 172.

Distal movement of the third drive member 172 effectuates a second function of an end effector operably secured to the adapter assembly 100 (FIG. 2). If, for example, the tool assembly 30 (FIG. 1) is operably secured to the adapter assembly 100 and the loading unit 40 (FIG. 1) is operably secured to the third drive member 172, distal movement of the third drive member 172 advances a pusher assembly (not shown) to effectuate the stapling of tissue.

Figure 15:
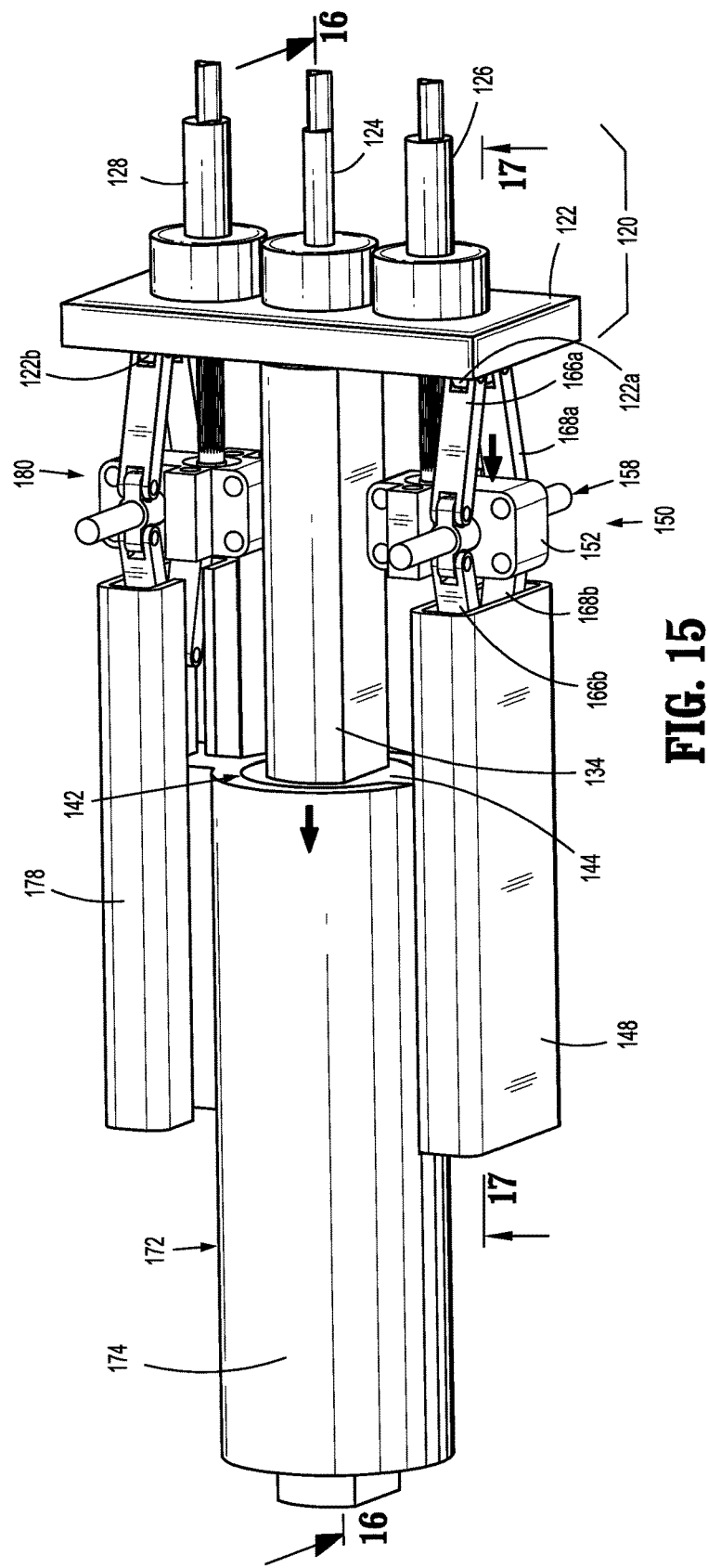
FIG. 15 is a perspective top view of the drive assembly of FIG. 3 with the first drive sub-assembly in the retracted position and each of the second and third drive sub-assemblies in the extended position.
Figure 16:
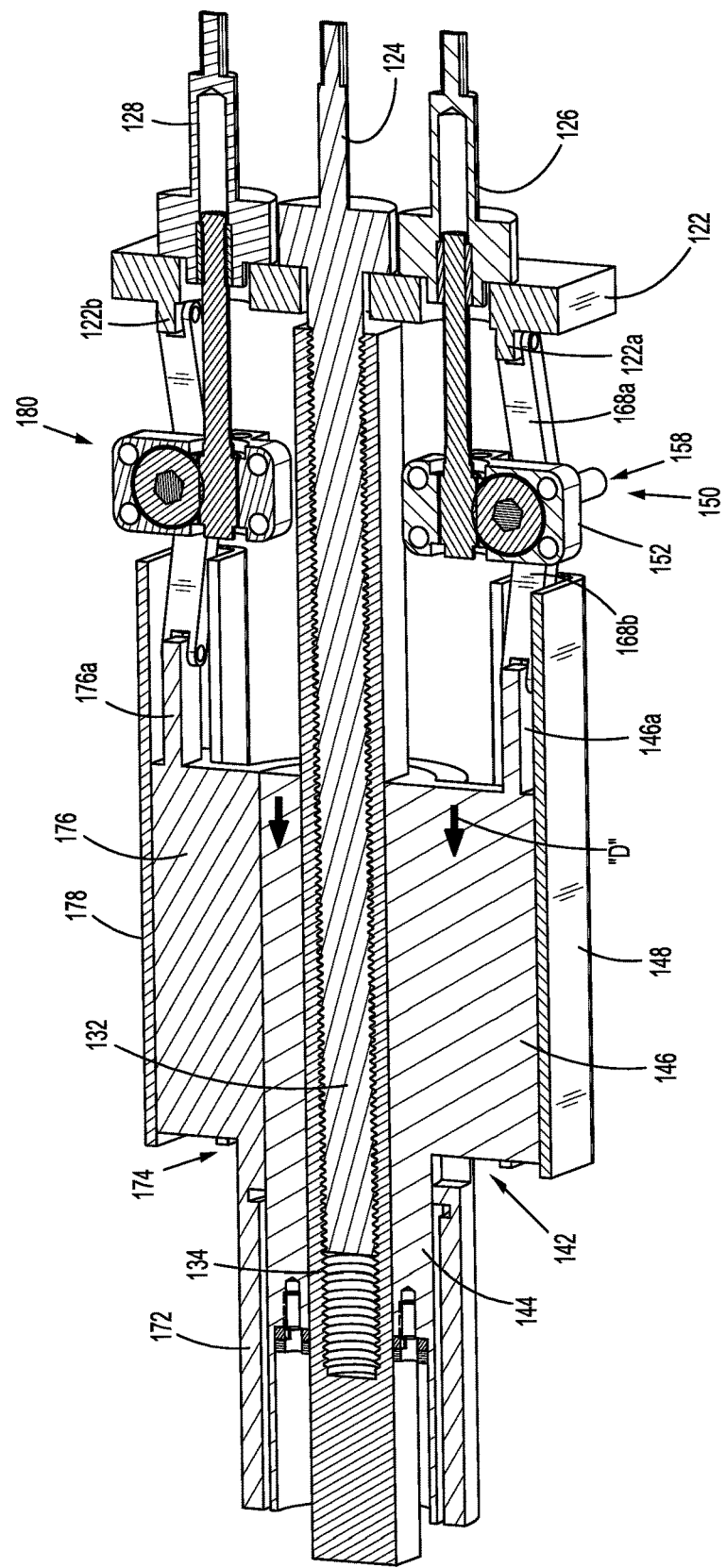
FIG. 16 is a cross-sectional top view of the drive assembly of FIG. 3 taken along line 16-16 of FIG. 15.
Figure 17:
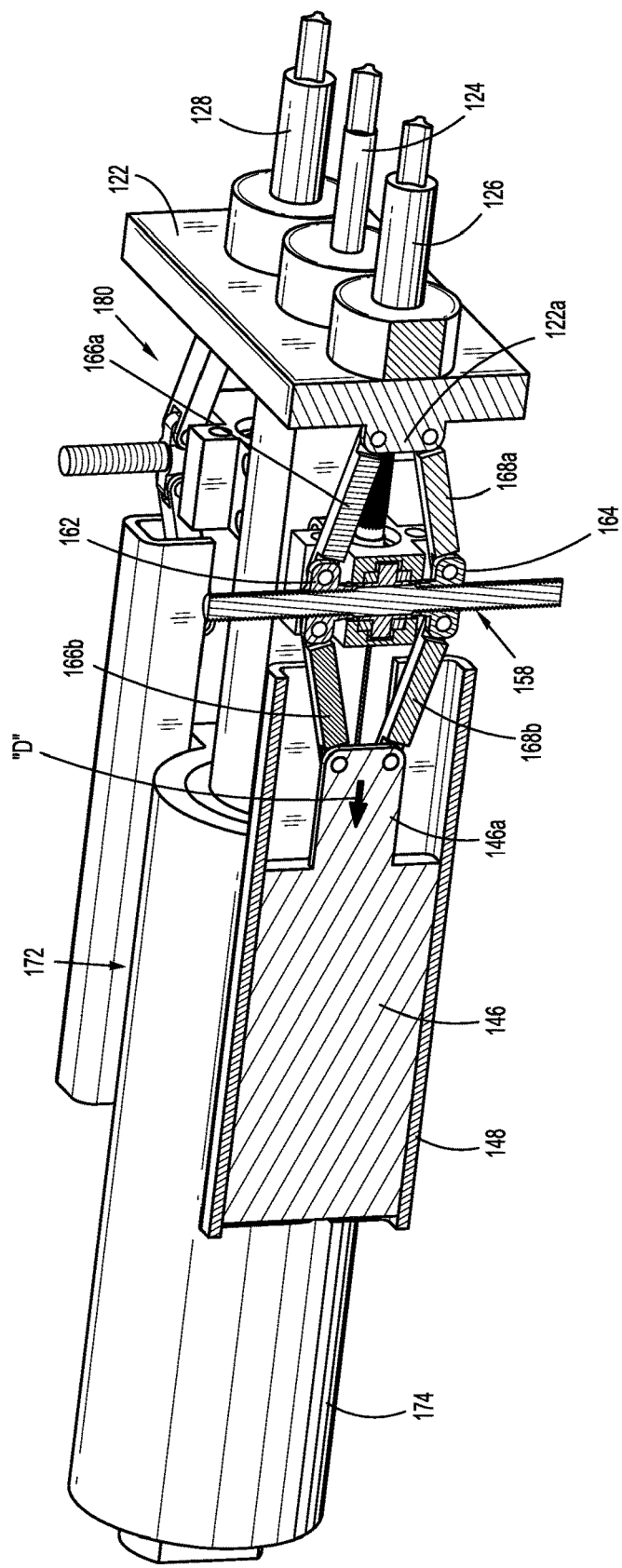
FIG. 17 is a cross-sectional side view of the drive assembly of FIG. 3 taken along line 17-17 of FIG. 15.

Turing now to FIGS. 15-17, movement of the second drive assembly 140 from the first position (FIG. 8) to a second, extended position is effected by operation of the surgical device 10 (FIG. 1). Specifically, rotation of the second shaft (not shown) of the surgical device 10 (FIG. 1) causes rotation of the second connector member 126 of the drive coupling assembly 120. As the second connector member 126 rotates in a first direction, the first drive shaft 154 of the first jackscrew assembly 150 rotates in the same first direction. Rotation of the first drive shaft 154 causes rotation of the jackscrew 158 of the first jackscrew assembly 150. As the jackscrew 158 rotates, the first and second jackscrew carriers 162, 164 of the first jackscrew assembly 150 move from the position on the extreme ends of the jackscrew 158 towards each other and the housing 152 of the first jackscrew assembly 150.

As the first and second jackscrew carriers 162, 164 move towards the housing 152 the angle between the first and second links 166a, 166b, 168a, 168b of respective first and second link assemblies 166, 168 of the second jackscrew assembly 150 increases, thereby increasing the effective length of the second jackscrew assembly 150 and causing the second drive member 142 of the second drive assembly 140 to move distally, as indicated by arrow "D" in FIG. 16. Conversely, when the second connector member 126 is rotated in a second direction, the drive shaft 152 rotates in the second direction to cause the jackscrew 158 to turn in the second direction which moves the first and second jackscrew carriers 162, 164 away from the housing 142 thereby causing the second drive member 142 to move proximally, i.e., retract. As noted above, the guide member 148 maintains the second drive member 142 in axial alignment with the longitudinal axis "x" (FIG. 2) of the adapter assembly 100 (FIG. 2) during translation of the second drive member 142.

Distal movement of the second drive member 142 effectuates a third function. If, for example, the tool assembly 30 (FIG. 1) is operably secured to the adapter assembly 100 (FIG. 2) and the loading unit 40 (FIG. 1) is operably secured to the second drive member 142, distal movement of the second drive member 142 advances a knife assembly to effectuate the cutting of tissue.

Although the drive assembly 115 (FIG. 3) of the adapter assembly 100 (FIG. 1) has been shown and described as relates to operation of the tool assembly 30 (FIG. 1) including the loading unit 40 (FIG. 1) and the anvil assembly 50 (FIG. 1), the drive assembly 115 may be modified for operation with end effectors having different configurations. For example, the drive assembly 115 may be modified for use with an end effector having only a single actuation, e.g., linear stapling.

Any of the components described herein may be fabricated from either metals, plastics, resins, composites or the like taking into consideration strength, durability, wearability, weight, resistance to corrosion, ease of manufacturing, cost of manufacturing, and the like.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An adapter assembly for operably connecting an end effector to an electromechanical surgical instrument, the adapter assembly comprising:
a drive coupling assembly configured for releasable connection to the electromechanical surgical instrument;
a first drive assembly operably connected to the drive coupling assembly, the first drive assembly including a drive screw;
a second drive assembly operably connected to the drive coupling assembly, the second drive assembly including a first jackscrew assembly; and
a third drive assembly operably connected to the drive coupling assembly, the third drive assembly including a second jackscrew assembly.

2. The adapter assembly of claim 1, wherein the second drive assembly includes a second drive member operably connected to the first jackscrew assembly, the first jackscrew assembly being movable from a collapsed configuration to an extended configuration to move the second drive member from a proximal position to a distal position.

3. The adapter assembly of claim 2, wherein the third drive assembly includes a third drive member operably connected to the second jackscrew assembly, the second jackscrew assembly being movable from a collapsed configuration to an extended configuration to move the third drive member from a proximal position to a distal position.

4. The adapter assembly of claim 3, wherein each of the second and third drive members includes a tubular portion, the tubular portion of the third drive member being slidably disposed within the tubular portion of the second drive member.

5. The adapter assembly of claim 4, wherein each of the second and third drive assemblies includes a guide member, and each of the second and third drive members include a guide portion slidably disposed within the respective guide members.

6. The adapter assembly of claim 4, wherein the first drive assembly includes a first drive member, the first drive member being slidably disposed within the tubular portion of the second drive member.

7. The adapter assembly of claim 1, wherein the drive coupling assembly includes a thruster plate and first, second, and third connector members.

8. The adapter assembly of claim 7, wherein the first connector member is operably connected to the drive screw, the second connector member is operably connected to the first jackscrew assembly, and the third connector member is operably connected to the second jackscrew assembly.

9. The adapter assembly of claim 1, wherein the first jackscrew assembly includes a housing, a drive shaft rotatably received within the housing, a worm drive operably disposed on the drive shaft, a jackscrew received within the housing and extending perpendicular to the drive shaft, a worm gear operably disposed about the jackscrew, first and second jackscrew carriers operably received on the jackscrew, and first and second link assemblies pivotally connected to the respective first and second jackscrew carriers.

10. The adapter assembly of claim 1, wherein the first jackscrew assembly includes first and second link assemblies, each of the first and second link assemblies including first and second links, the first and second links of each of the first and second link assemblies defining a first angle therebetween when the first jackscrew assembly is in a collapsed configuration.

11. The adapter assembly of claim 10, wherein the first and second links of each of the first and second link assemblies define a second angle therebetween when the first jackscrew assembly is in an extended configuration.

12. The adapter assembly of claim 11, wherein the second angle is greater than the first angle.

13. The adapter assembly of claim 11, wherein the first jackscrew assembly defines a first effective length when the first jackscrew assembly is in the collapsed configuration and the first jackscrew assembly defines a second effective length when the first jackscrew assembly is in the extended configuration, the second effective length being greater than the first effective length.

14. The adapter assembly of claim 1, further including a rotation assembly including a base and a rotation handle rotatably secured to the base.

15. The adapter assembly of claim 14, further including a sleeve fixedly secured to the rotation handle.

16. The adapter assembly of claim 15, wherein the first, second, and third drive assemblies are secured within the base.

17. An adapter assembly for operably connecting an end effector to an electromechanical surgical instrument, the adapter assembly comprising:
   a drive coupling assembly;
   a first drive assembly operably connected to the drive coupling assembly, the first drive assembly including a first jackscrew assembly; and
   a second drive assembly operably connected to the drive coupling assembly, the second drive assembly including a second jackscrew assembly, wherein the first and second jackscrew assemblies operate independent of one another.

18. The adapter assembly of claim 17, further including a third drive assembly operably connected to the drive coupling assembly, the third drive assembly including a drive screw.

19. An adapter assembly for operably connecting an end effector to an electromechanical surgical instrument, the adapter assembly comprising:
   a drive coupling assembly configured for releasable connection to the electromechanical surgical instrument;
   a first drive assembly operably connected to the drive coupling assembly, the first drive assembly including a first jackscrew assembly; and
   a second drive assembly operably connected to the drive coupling assembly, the second drive assembly including a second jackscrew assembly.

20. The adapter assembly of claim 19, further including a third drive assembly operably connected to the drive coupling assembly, the third drive assembly including a drive screw.

* * * * *